United States Patent [19]
Lenker et al.

[11] Patent Number: 6,078,832
[45] Date of Patent: Jun. 20, 2000

[54] LESION MEASUREMENT CATHETER AND METHOD

[75] Inventors: Jay A. Lenker, Los Altos Hills; Rodney A. White, San Pedro; Richard Murphy, Mountain View; Steve Kim, Sunnyvale, all of Calif.

[73] Assignee: Medtronic, Inc., Minneapolis, Minn.

[21] Appl. No.: 09/167,997

[22] Filed: Oct. 7, 1998

Related U.S. Application Data

[62] Division of application No. 08/757,413, Nov. 27, 1996, Pat. No. 5,860,923, which is a continuation of application No. 08/380,735, Jan. 30, 1995, abandoned.

[51] Int. Cl.$^7$ .................................................. A61B 6/00
[52] U.S. Cl. ............................................ 600/433; 600/585
[58] Field of Search ................................ 600/433, 434, 600/585; 604/95, 96, 280

[56] References Cited

U.S. PATENT DOCUMENTS

| | | | |
|---|---|---|---|
| 4,133,303 | 1/1979 | Patel | 128/2 S |
| 5,045,071 | 9/1991 | McCormick et al. | 604/280 |
| 5,054,492 | 10/1991 | Schribner et al. | 128/662.06 |
| 5,209,730 | 5/1993 | Sullivan | 604/96 |
| 5,239,982 | 8/1993 | Trauthen | 128/4 |
| 5,263,928 | 11/1993 | Trauthen et al. | 604/53 |
| 5,275,169 | 1/1994 | Afromowitz et al. | 128/673 |
| 5,364,354 | 11/1994 | Walker | 604/96 |
| 5,419,324 | 5/1995 | Dillow | 128/653.1 |
| 5,484,449 | 1/1996 | Amundson et al. | 606/108 |
| 5,507,726 | 4/1996 | Johnson et al. | 604/96 |
| 5,578,018 | 11/1996 | Rowland et al. | 604/280 |

FOREIGN PATENT DOCUMENTS

WO 95/14501  6/1995  WIPO ........................ A61M 29/00

OTHER PUBLICATIONS

Chuter, T. et al., "Anatomy of the Infrarenal Aortic Aneurysm," *Endoluminal Vascular Prostheses* pg. 21–36; Little, Brown and Company; Boston (1995).

Chuter, T. et al., "Patient Selection and Preoperative Assessment, "*Endoluminal Vascular Prostheses* pg 255–283; Little, Brown and Company; Boston (1995).

*Primary Examiner*—Cary O'Connor
*Assistant Examiner*—Pamela Wingood

[57] ABSTRACT

The invention provides methods and apparatus for determining physiological characteristics of body lumens, such as the length of a blood vessel. According to one exemplary method, the distance between a first target location and a second target location within a lumen are measured by aligning a first marker on a first elongate member disposed within a lumen with the first target location. A second marker on a second elongate member disposed within the lumen is aligned with the second target location. The distance between the first and second markers is then measured, and the measured distance corresponds to the distance between the first and second target locations.

18 Claims, 13 Drawing Sheets

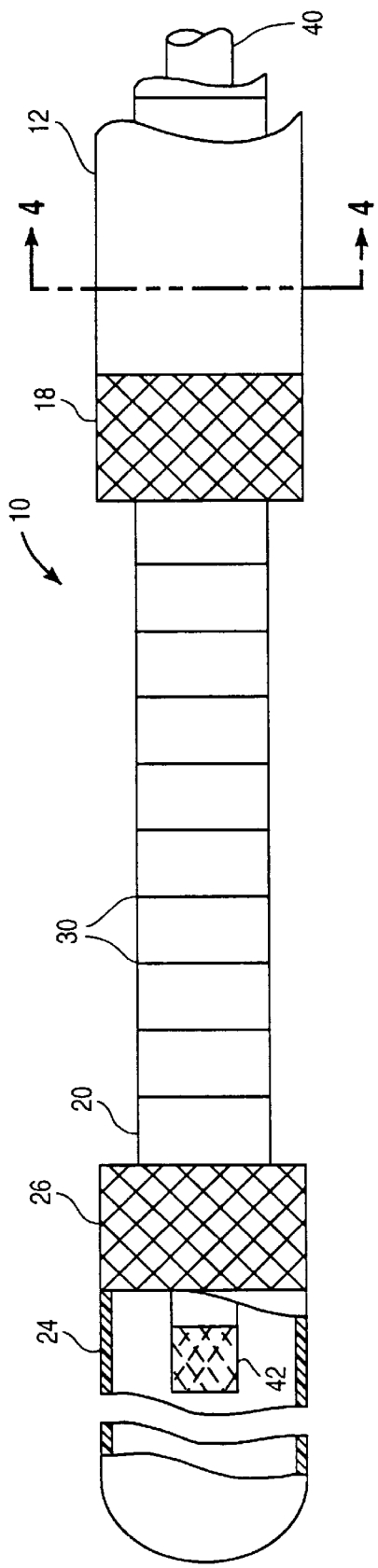
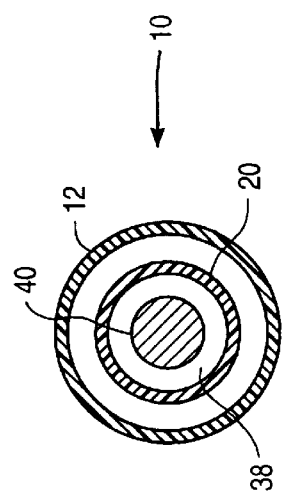
FIG. 3
FIG. 4

LESION MEASUREMENT CATHETER AND METHOD

CROSS-REFERENCE TO RELATED APPLICATIONS

This application is a divisional of U.S. patent application Ser. No. 08/757,413, filed Nov. 27, 1996 now U.S. Pat. No. 5,860,923 which is a continuation of U.S. patent application Ser. No. 08/380,735, filed Jan. 30, 1995, the full disclosures of which are incorporated herein by reference.

BACKGROUND OF THE INVENTION

1. Field of the Invention

The present invention relates generally to the field of medical diagnostics, and particularly to the field of determining physiologic characteristics of body lumens. In one particular aspect, the invention provides methods and apparatus for measuring the length of vascular lesions.

To properly treat many bodily diseases or abnormalities, certain physiologic characteristics, such as the size of a particular body member, often need to be determined. One example is in the treatment of vascular lesions, and particularly vascular aneurysms, which often requires the endoluminal placement of tubular prostheses, such as grafts, stents, and other structures. Before the prosthesis is placed in the vascular anatomy, the size of the lesion is measured so that a properly sized prosthesis can be selected.

Vascular aneurysms are the result of abnormal dilation of a blood vessel, usually resulting from disease and/or genetic predisposition which can weaken the arterial wall and allow it to expand. While aneurysms can occur in any blood vessel, most occur in the aorta and peripheral arteries, with the majority of aortic aneurysms occurring in the abdominal aorta, usually beginning below the renal arteries and often extending distally into one or both of the iliac arteries.

Aortic aneurysms are most commonly treated in open surgical procedures where the diseased vessel segment is by-passed and repaired with an artificial vascular graft. Recently, methods for endovascular graft placement for the treatment of aneurysms have been proposed. One such method and apparatus for endovascular placement of intraluminal prostheses, including both grafts and stents, is described in co-pending U.S. patent application Ser. No. 08/290,021, filed Aug. 12, 1994, the disclosure of which is herein incorporated by reference. A suitable intraluminal prosthesis for such a method includes a radially compressible, tubular frame having a proximal end, a distal end, and an axial lumen therebetween. The prosthesis is delivered to the area of interest via a delivery catheter. The prosthesis is then partially released from the catheter into a blood vessel or other body lumen to allow the prosthesis to radially expand and conform to the interior surface of the lumen being treated. The prosthesis can then be repositioned by the catheter until it is properly placed within the vessel. Other exemplary graft prostheses are described in co-pending U.S. patent application Ser. No. 08/255,681, the disclosure of which is herein incorporated by reference.

As previously described, before the endoluminal placement of an intraluminal prosthesis, it is desirable to first determine the appropriate size for the prosthesis so that the prosthesis will properly fit within the body lumen. For instance, in the case of vascular aneurysms, it is desirable to determine the length of the aneurysm so that the prosthesis will be long enough to extend through the diseased area of the vessel. In this way, both ends of the prosthesis can be attached to a healthy vessel wall. Current methods for determining the length of an effected body lumen employ fluoroscopy. To determine the length of a vessel using fluoroscopy, a catheter is inserted into the vessel and a contrast agent is injected into the vessel through the catheter. The blood flow carries the contrast agent along the vessel so that the vessel can be radiographically imaged with a fluoroscope. The fluoroscope produces a planar (or two dimensional) image of the vessel which can be evaluated to determine the existence of a diseased or abnormal area within the vessel. The length of the diseased or abnormal area is then estimated by measuring the length of the diseased area on the radiographic image. However, the length of such a measurement is typically not particularly accurate since it relies on discerning an ill-defined boundary in a single plane. Such a measurement does not take into account that the vessel is usually not in the same plane as the resulting fluoroscopic image. Hence, measurement of the body lumen using only a two-dimensional image can produce a length that is significantly less than the actual length of the body lumen. Another drawback to using such procedures to determine the length of a vessel is that the vessel is often non-linear, i.e. does not extend in a straight line. Hence, even if the vessel were in the same plane as the resulting fluoroscopic image of the vessel, it would still be difficult to measure the length of a curving vessel.

Improper determination of the vessel size can result in the selection of a prosthesis that is too short and hence cannot be properly grafted. The endoluminal placement of an improperly sized prosthesis can present a number of serious problems. One problem is that the prosthesis must be removed from the body lumen and replaced with another that is properly sized. This can often be difficult if the prosthesis has been radially expanded while in the body lumen. To remove the expanded prosthesis, the prosthesis must be radially compressed and then withdrawn from the body lumen. Such a procedure increases the risk of injury to the patient as well as unduly increasing operating time and expense.

Methods and apparatus are therefore needed for accurately measuring the length of a body lumen, and in particular the length of a vascular lesion. In one particular aspect, it would be desirable to provide improved methods and apparatus for the measurement of vascular aneurysms so that the proper size of intraluminal prostheses, such as grafts and stents, can be accurately determined. It would be further desirable if such methods and apparatus were simple to use and could be used with existing fluoroscopy technology.

2. Description of the Background Art

As previously described, methods and apparatus for placement and repositioning of intraluminal prostheses are described in U.S. patent application Ser. No. 08/290,021, the disclosure of which has previously been incorporated by reference. Suitable graft structures for placement in body lumens are described in U.S. patent application Ser. No. 08/255,681, the disclosure of which has previously been incorporated herein by reference.

U.S. Pat. No. 5,275,169 describes methods and apparatus for determining the internal cross-sectional area and diameter of a vessel.

SUMMARY OF THE INVENTION

The present invention provides methods and apparatus for determining physiologic characteristics of body lumens, and particularly for determining the length of target regions within body lumens. Body lumens amenable to the methods and apparatus of the present invention include blood vessels, the intestines, the urethra, and the like. Although suitable for the physiologic measurement of most body lumens, the present invention will find its greatest use in the measurement of vascular lesions, particularly vascular aneurysms, and in the measurement of other vascular blockages. Advantageously, the measurement of such physiologic characteristics can be used to select the proper length of intraluminal prostheses, such as grafts and stents, the proper balloon size for balloon angioplasty procedures, and the proper size of other therapeutic devices.

According to the present invention, a method is provided for measuring the distance between a first target location and a second target location within a lumen. According to the method, a first marker on a first elongate member disposed within the lumen is aligned with the first target location. A second marker on a second elongate member disposed within the lumen is aligned with the second target location. The distance between the first and second markers is then measured, with the measured distance corresponding to the distance between the first and the second target locations. In one particular aspect, the lumen is non-linear, i.e. does not extend in a straight line, and the distance between the first and second markers is measured substantially along a center line of the lumen, i.e. a line extending axially through the center of the lumen, to provide a measurement of the lumen's length.

In an exemplary aspect, the lumen is a blood vessel lumen and the first and second target locations correspond to the ends of a lesion. In this way, the length of the lesion can be determined by the distance between the first and second target locations. In a further aspect, each marker is aligned with its target location by manually translating the elongate members carrying the markers within the lumen. In still a further aspect, the first and second markers are radiopaque and the lumen is fluoroscopically imaged to produce fluoroscopic images of the markers. The markers are then aligned by visually aligning the fluoroscopic images of the markers with the ends of the lesion. Alternatively, the first and second markers are ultrasonically opaque and the lumen is intraluminally ultrasonically imaged to produce an ultrasonic image of the markers. The markers are then aligned with the target locations by aligning the ultrasonic images of each market with one end of the lesion.

The measuring of the distance between the first and second markers will preferably be performed by visually observing calibration marks on one member relative to a reference location on the other member. The calibration marks can be observed while the members remain disposed in the lumen, or alternatively after the members are withdrawn from the lumen. If the members are withdrawn from the body lumen prior to measuring the distance between the markers, the elongate members will preferably be locked together after alignment with their respective markers so that the distance between the markers will remain the same while the members are withdrawn from the lumen.

In a particularly preferable aspect, the length of a vascular graft or stent is selected based on the distance measured between the two markers. In this way, the length of the graft or stent can be selected so that it is sufficiently long to extend over the length of the lesion.

The invention provides a luminal lesion measurement catheter which includes a first elongate member having a proximal end, a distal end, and a radiopaque marker near the distal end. A second elongate member is provided and is slidably received relative to the first member. The second elongate member includes a proximal end, a distal end, and a radiopaque marker near the distal end. The second member has a length that is greater than the length of the first member and has axially spaced-apart calibration marks which permit direct visual reading of the axial distance between the radiopaque markers on the first and second members.

In one particular aspect, the first member is a tubular sleeve having a central passage and a sealing valve at its proximal end. The length of the tubular sleeve is preferably in the range from about 40 cm to 200 cm. In another aspect, the second member is a tubular body having a central guidewire lumen and a length in the range from about 41 cm to 220 cm. In an exemplary aspect, the calibration marks are visible on the outside surface of the tubular body. In still another aspect, the calibration marks are at the distal end of the tubular body. Alternatively, the calibration marks are at the proximal end of the tubular body.

In one particular embodiment, a third elongate member is provided and is slidably received relative to both the first and second members. The third member has a proximal end, a distal end, and a central lumen for receiving the first and second members. In one aspect, at least one balloon is provided on the third elongate member for centering the third member within a blood vessel lumen. In another embodiment, the balloon is attached both to the distal end of the third member and to a position near the distal end of the second member. In this way, inflation media can be introduced to the balloon through the central lumen of the third member. In a particular aspect, the third member is radially expandable near its distal end for centering the third member within a blood vessel lumen.

The invention provides a further embodiment of a luminal lesion measurement catheter. The catheter includes an elongate catheter body having a proximal end, a distal end, and a central lumen. A balloon is disposed around the catheter body near the distal end. The balloon can be constructed of either an elastic or an inelastic material. About the periphery of the balloon are a plurality of spaced-apart concentric markers, with the markers being radio or fluoroscopically opaque and/or visible by ultrasound. In a preferable aspect, the markers are equally spaced-apart on the balloon and have a constant width. In this manner, the markers can be ultrasonically or fluoroscopically imaged when the balloon is positioned within a body lumen and inflated. From the resulting image, the number of markers between the ends of the lesion can be counted to determine the length of the lesion. Additionally, the diameter of the balloon can be determined from the image. Further, the radius of curvature of the balloon throughout the lesion can be determined by evaluating the orientation of the markers. In this way, a three dimensional model of the lesionous area can be produced allowing for an accurate size selection of a prosthetic device.

BRIEF DESCRIPTION OF THE DRAWINGS

FIG. 3 illustrates a more detailed view of one particular embodiment of a distal end of the catheter of FIG. 2.

FIG. 4 is a cross-sectional view of the catheter of FIG. 3 taken along lines 4—4.

DETAILED DESCRIPTION OF THE SPECIFIC EMBODIMENT

The present invention provides methods and apparatus for determining physiologic characteristics, such as the internal axial length, of a body lumen. The methods and apparatus will preferably be used to measure the length of vascular lesions, and will find its greatest use in measuring the length of vascular aneurysms. The methods and apparatus can also find use in measuring physiologic characteristics of other defects or abnormalities such as the size of vascular blockages. Length measurements provided by the present invention will be particularly useful in sizing intraluminal prostheses, such as vascular grafts or stents, that are endovascularly placed within the vessel to treat the aneurysm or other abnormality. Length measurements provided by the invention can also be used to select the proper length of a balloon on a balloon angioplasty catheter or to size other therapeutic devices.

An important feature of the present invention is that it allows for physiologic characteristics to be measured regardless of the orientation of the body lumen within the body. Usually, most body lumens curve throughout the body thereby reducing the accuracy of length measurements obtained from conventional fluoroscopy procedures which produce planar images of the lumen. The present invention takes into consideration the varied orientations of body lumens within the body when determining their physiologic characteristics. In making such determinations, the present invention can incorporate the use of existing fluoroscopy technology as well as existing ultrasonic imaging technology.

Figure 1:
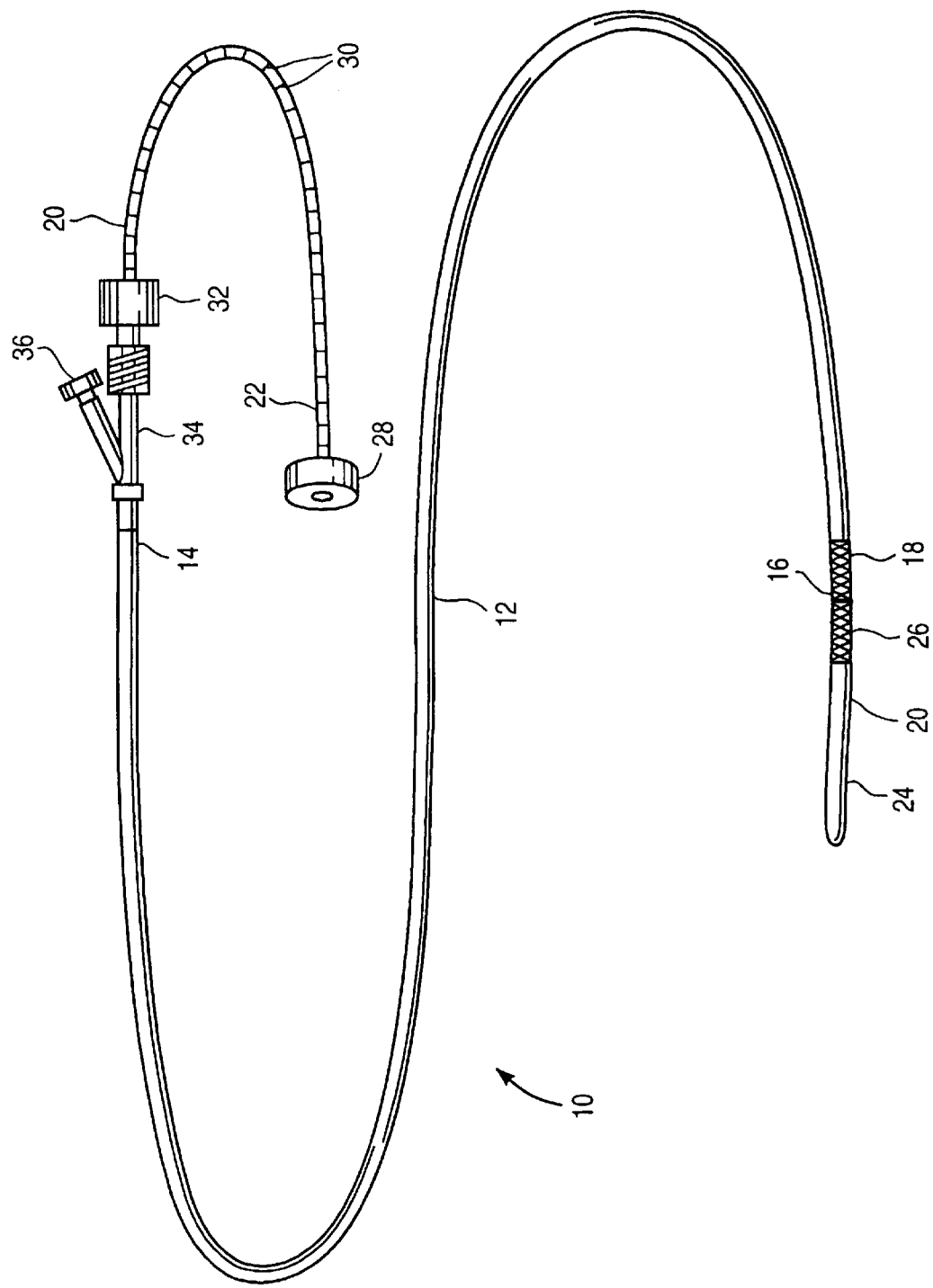
FIG. 1 illustrates an exemplary embodiment of a luminal lesion measurement catheter according to the present invention. The catheter is shown in a closed position with two radio opaque markers that are adjacent each other.
Figure 2:
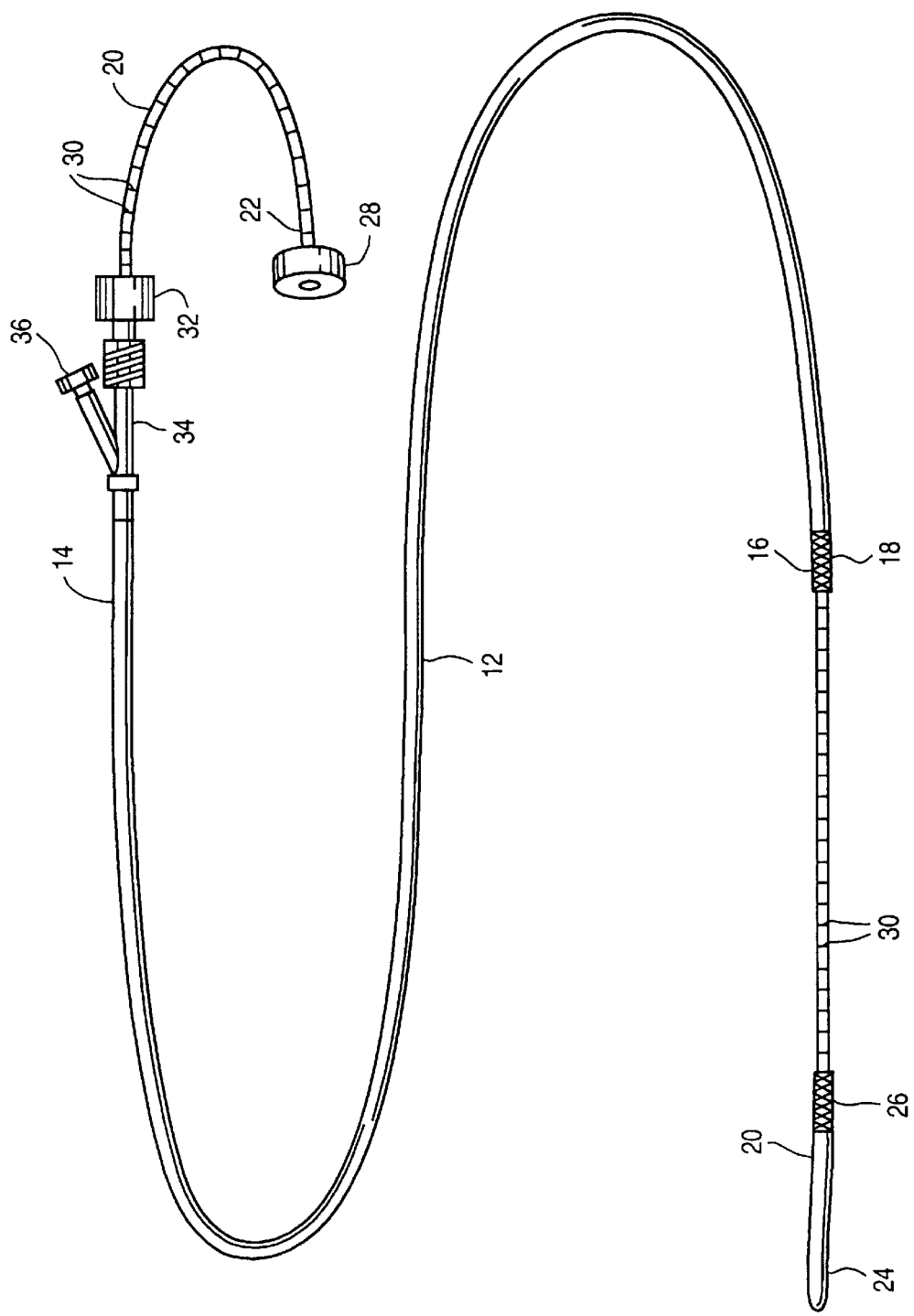
FIG. 2 illustrates the catheter of FIG. 1 in a measuring position where the two radiopaque markers are separated to permit direct visual reading of the axial distance between two radiopaque markers.

To provide such features and advantages, the invention in one exemplary embodiment provides a luminal lesion measurement catheter 10 as shown in FIG. 1. The catheter 10 includes a first elongate member 12 having a proximal end 14 and a distal end 16. A radiopaque marker 18 is provided at the distal end 16. The first elongate member 12 is preferably tubular for slidably receiving a second elongate member 20. The second elongate member 20 has a proximal end 22 and a distal 24. Near the distal end 24 is another radiopaque marker 26. The first and second elongate members 12, 20 are slidable relative to each other. The radiopaque markers 18, 26 are positioned adjacent each other. With this configuration, the catheter 10 is in a closed position. As shown in FIG. 2, the second elongate member 20 can be slid relative to the first member 12 to separate the markers 18, 26 and to place the catheter 10 in a measurement position. The distal end 24 of the second member 20 has a cross-sectional dimension that is equal to or greater than the remaining proximal length of the second member 20. In this way, the distal end 24 serves as a stop to prevent the proximal travel of the second member 20 through the first member 12 when the markers 18, 26 become adjacent to each other. The second member 20 has a length greater than the length of the first member 12 so that the distal end 24 of the second member 20 can be slid in a distal direction away from the radiopaque marker 18 while the proximal end 22 of the second member 20 remains without the first member 12 at all times. A pull knob 28 is provided at the proximal end 22 of the second member 20 to assist in the translation of the second member 20 relative to the first member 12 and also to serve as a stop to prevent further distal translation of the second member 20 relative to the first member 12.

Provided on the second member 20 are a plurality of axially spaced-apart calibration marks 30. The calibration marks 30 can be spaced-apart by any distance, and can be varied depending on the precision needed for the particular application. The marks 30 can be provided along the entire length of the second member 20 that is proximal to the marker 26, or can alternatively be provided only near the distal end 24 and just proximal to the marker 26, only the proximal end 22, or both. Providing calibration marks 30 near the marker 26 (see FIG. 2) allows for direct visual reading of the axial distance between the radiopaque markers 18, 26 from the distal end of the catheter 10, while providing calibration marks 30 at the proximal end 22 allows for direct visual reading of the axial distance between the radiopaque markers 18, 26 from a proximal end of the catheter 10. Inclusion of the calibration marks 30 at the proximal end 22 is advantageous in that the axial distance between the markers 18, 26 can be determined while the catheter 10 is within a patient because the proximal end 22 remains outside the patient at all times. To visually read the marks 30 near the distal end 24 while the catheter remains in the patient, the marks can be radiopaque and visualized fluoroscopically. Alternatively, the catheter 10 can be removed from the patient to visualize the marks 30 near the distal end 24.

Determination of the axial distance between the markers 18, 26 from the distal end of the catheter 10 is performed by counting the number of calibration marks 30 between the markers 18, 26. In this way, the marker 18 serves as a reference marker. Conveniently, length reference numerals can be placed adjacent the marks 30 to indicate the axial distance. A valve 32 is provided at to the proximal end 14 of the first member 12 and in one aspect serves as a reference marker at the proximal end of the catheter 10. In this way, determination of the axial distance between the markers 18, 26 can be performed by counting the number of calibration marks 30 between the pull knob 28 and the valve 32, with fewer marks 30 indicating a longer axial distance. Conveniently, length reference numerals can be placed adjacent the marks 30 at the proximal end 22.

The valve 32 also serves as a sealing valve to prevent fluids from leaking through the first member 12 when the catheter 10 is inserted into the patient. The valve 32 will preferably be a tuohy borst. The valve 32 is connected to the proximal end 14 of the first member 12 via a connector 34. The connector 34 is optionally provided with an inflation port 36 which can be used to inflate a centering balloon as described in more detail hereinafter.

The catheter 10 will preferably be sized to have a length sufficient to reach the vascular anatomy of a patient. Preferably, the length of the first member 12 will be in the range from about 40 cm to 200 cm. The second member 12 will preferably have a length in the range from about 41 cm to 220 cm.

Construction of the catheter 10 will be described in greater detail with reference to FIGS. 3 and 4 where one particular embodiment of a distal end of the catheter 10 is shown. The first elongate member 12 is preferably constructed from a tubular sleeve and is sized to receive the portion of the second elongate member 20 that is proximal to the marker 26. As previously described, the distal end 24 of the second member 20 has a diameter equal to or greater than the diameter of the first member 12 to prevent proximal travel of the second member 20 relative to the first member 12 when the radiopaque markers 18, 26 become adjacent to each other.

The second elongate member 20 preferably includes a central guidewire lumen 38 for receiving a guidewire 40. The guidewire 40 is used as a guide to direct the catheter 10 to the desired area of the body lumen.

The radiopaque markers 18, 26 are provided as end points when measuring the length of a lesion in the body lumen, and particularly when measuring the length of a vascular aneurysm in a blood vessel. During fluoroscopy, the radiopaque markers 18, 26 remain visible allowing each marker 18, 26 to be aligned with each end of the aneurysm. Once the markers 18, 26 are aligned, the length of the aneurysm can be determined by reading the calibration marks 30.

To further augment imaging of the markers 18, 26 relative to the lesionous area, the guidewire 40 can optionally be provided with an ultrasonic imaging transducer 42. A suitable guidewire having an image transducer is described in U.S. patent application Ser. No. 5,095,911, the disclosure of which is herein incorporated by reference. Use of the ultrasonic imaging transducer 42 assists in locating anatomical landmarks in the vessel such as the end points of the aneurysm. The markers 18, 26 can be made to be ultrasonically opaque so that an ultrasonic image of the markers 18, 26 can also be produced. The markers 18, 26 can then be aligned with the end points by aligning their ultrasonic images. In a further alternative, the guidewire lumen 38 can be sized sufficiently to house both a conventional guidewire 40 and a separate ultrasonic transducer. In this way, the guidewire 40 can be used to direct the catheter 10 to the area of interest, and the transducer used to assist in aligning the markers 18, 26 with the end points of the aneurysm.

The first and second elongate members 12, 20 will preferably include a locking mechanism (not shown) for securing the members relative to each other. The locking mechanism can be selected from any of a number of locking mechanisms including a thumb screw, a clamp, a threaded connection, a cap and inwardly expandable donut, and the like, and will preferably be at the proximal end of the catheter. Use of such a locking mechanism is advantageous when the calibration marks 30 near the distal end 24 of the second elongate member 20 are used to determine the axial distance between the markers 18, 26. Once the markers 18, 26 are properly aligned, the locking mechanism can be secured and the entire catheter 10 removed from the patient. In this way, the markers 18, 26 remain spaced-apart at the appropriate distance after the catheter 10 has been removed from the patient.

Figure 5:
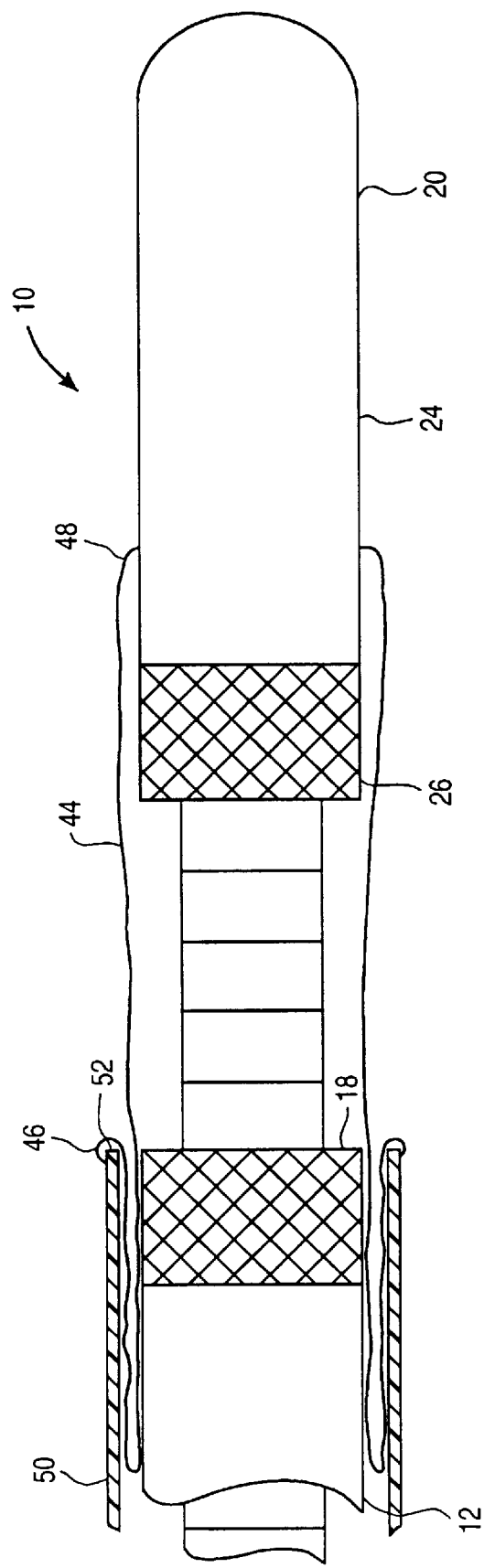
FIG. 5 illustrates a distal end of an alternative embodiment of a luminal lesion measuring catheter having a centering balloon at its distal end.

Due to the non-linear nature of many body lumens, it is often desirable to measure the length of the body lumen along a center line extending axially through the center of the body lumen. Such a measurement is useful in the selection of an appropriately sized intraluminal prosthesis. Referring to FIG. 5, the catheter 10 is provided with a centering balloon 44 for centering the catheter 10 within the body lumen. The centering balloon 44 includes a proximal end 46 and a distal end 48. The proximal end 46 is attached to a third elongate member 50, which is preferably a tubular sleeve for slidably receiving the catheter 10. The distal end 48 of the balloon 44 is attached to the distal end 24 of the second elongate member 20. Inflation media for inflating the balloon 44 can be provided either through the inflation port 36 (see FIG. 1) or through the third elongate member 50. The balloon 44 will preferably be inelastic and be constructed of materials such as polyurethane. Alternatively, in some cases the balloon 44 can be constructed of latex. The balloon 44 will preferably have a nominal diameter corresponding to the diameter of the body lumen. In this way, the balloon 44 can be expanded to center the catheter 10 within the body lumen, thereby allowing the length of the lesionous area to be measured along the center of the body lumen.

The first and third elongate members 12, 50 will preferably be able to be secured relative to each other. In this manner, the catheter 10 can be inserted into the body lumen while entirely housed within the third member 50, with the balloon 44 being housed in the annular space between the first and third elongate members 12, 50. When the area of interest in the body lumen is reached, the catheter 10 can be advanced until the radiopaque marker 18 on the first member 12 reaches a distal end 52 of the third elongate member 50. The first and third elongate members 12, 50 can then be secured relative to each other and the second elongate member 20 advanced to place the radiopaque marker 26 at the opposite end of the lesionous area. While the second member 20 is being advanced, inflation media is provided to the balloon 44 to inflate the balloon and center the second elongate member 20 as it travels through the lesionous area.

Figure 6:
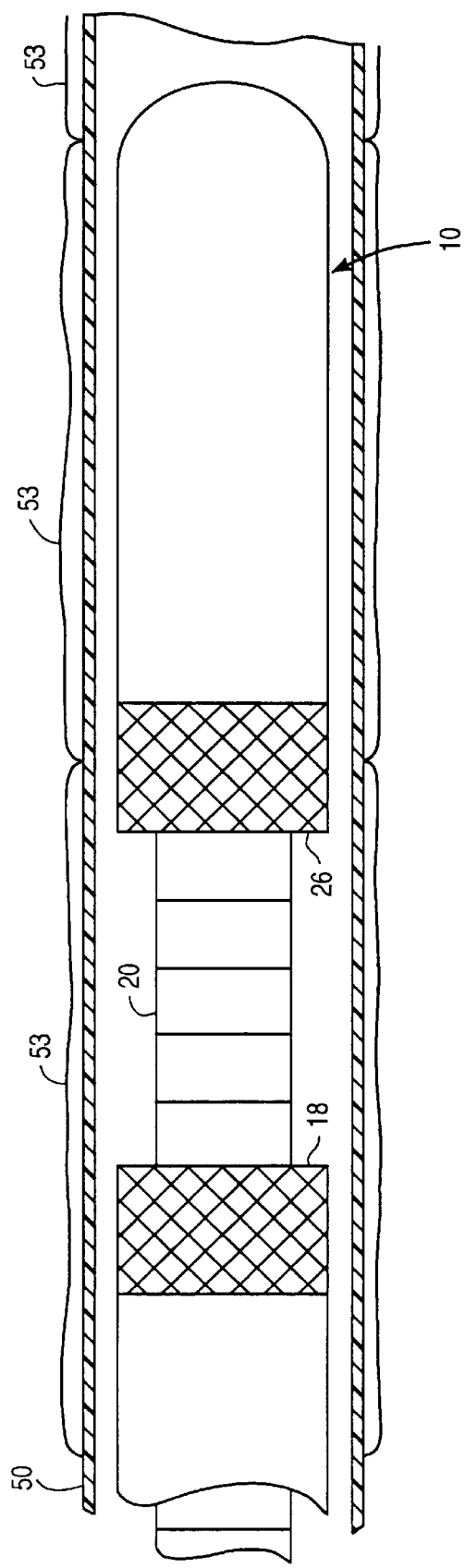
FIG. 6 illustrates a distal end of the catheter of FIG. 2 slidably held within an elongate tubular member having a plurality of centering balloons.

It will be appreciated that a variety of centering mechanisms can be employed, and the invention is not limited to only the use of balloon 44 to center the catheter 10 within the body lumen. For example, the third member 50 can be radially expandable (see FIG. 8) or can include a malecot which can be expanded in the body lumen to center the catheter 10. Alternative balloon arrangements can also be provided for centering the catheter 10 within the body lumen. For instance, the third elongate member 50 can be provided with a single balloon around its perimeter. As shown in FIG. 6, the third elongate member 50 can alternatively be provided with a plurality of balloons 53 about its periphery for centering the catheter 10. Use of the balloons 53 is advantageous in measuring lesions having large lengths and wide ranges of curvature.

When using a centering mechanism with the catheter 10, it may be desirable in some circumstances to ensure that blood flow through the vessel is not substantially hindered. When using a balloon as a centering device, the balloon can be provided with one or more perfusion lumens or external grooves for allowing blood flow through the balloon. In this way, blood can be allowed to travel through the vessel while the balloon is inflated.

Figure 7:
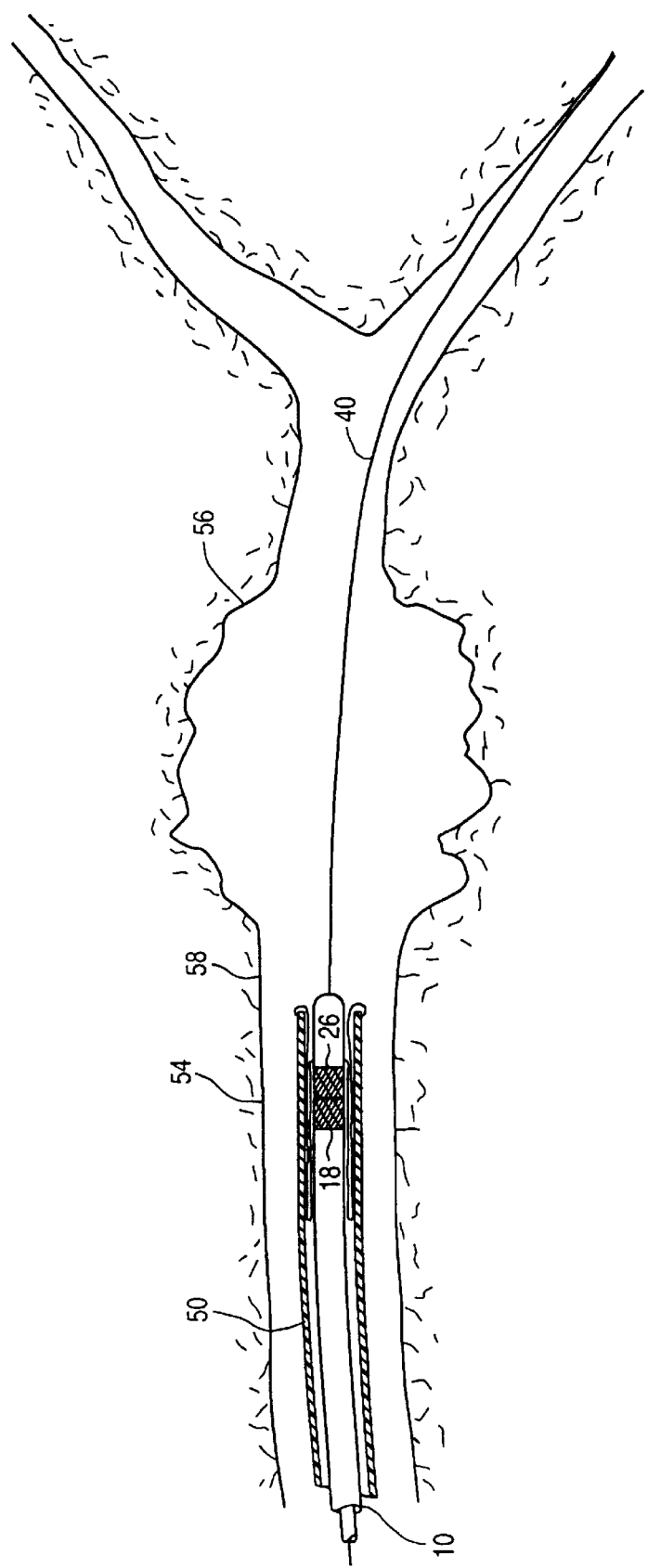
FIGS. 7–11 illustrate an exemplary method for measuring the length of lesion in a blood vessel according to the present invention.
Figure 8:
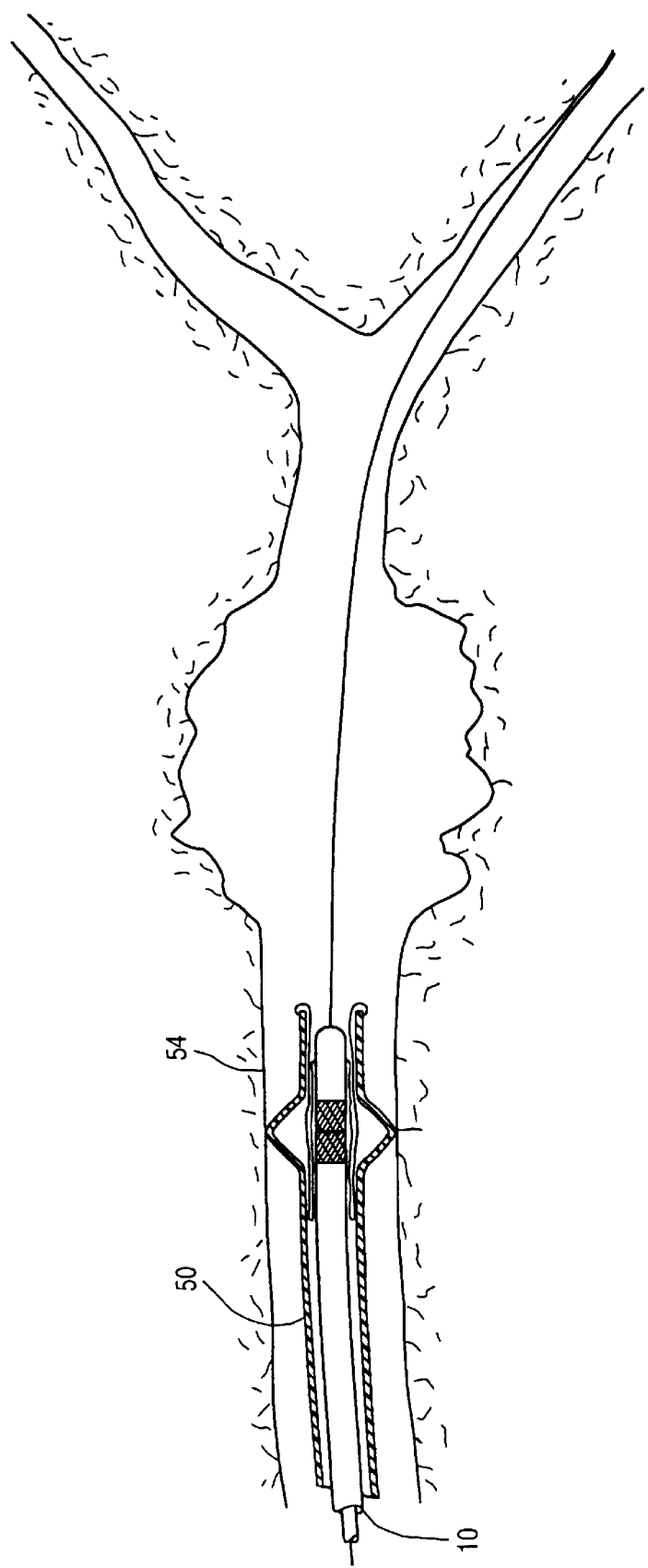
Figure 9:
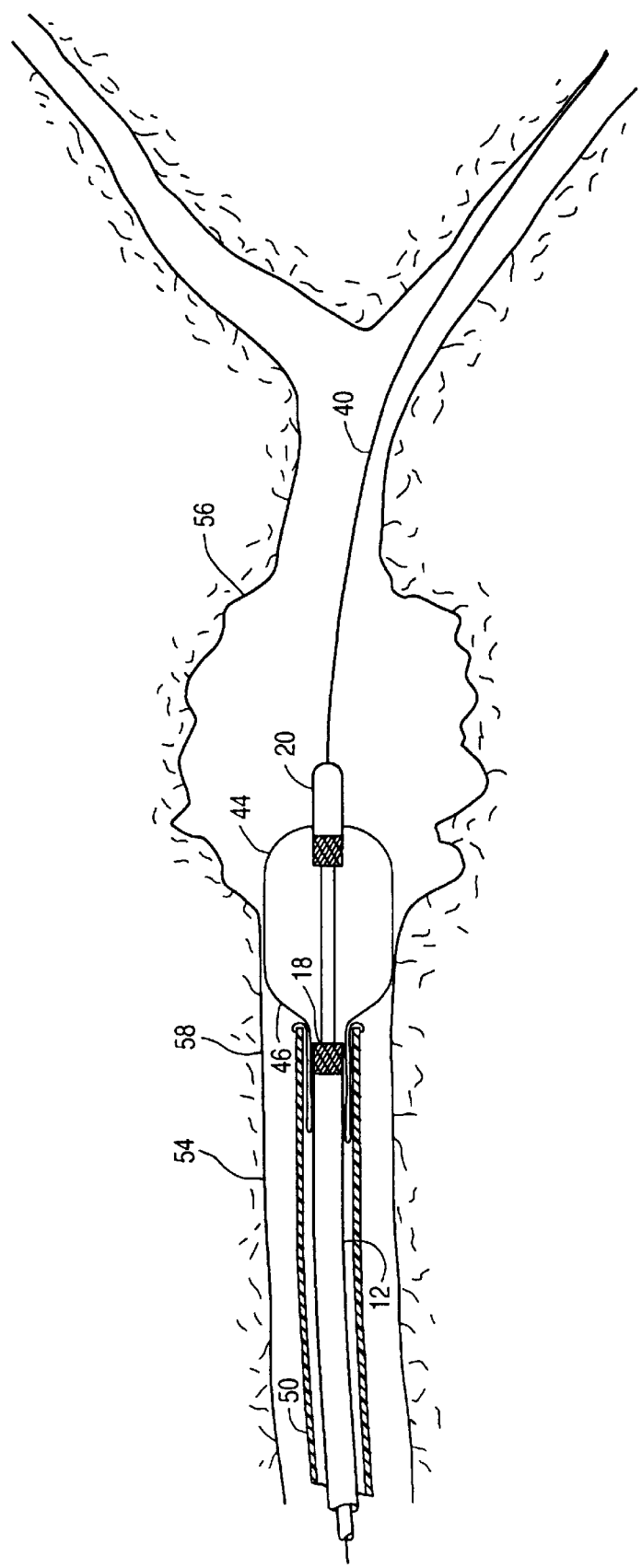

Referring to FIGS. 7–11, an exemplary method for measuring the length of a vascular aneurysm in a blood vessel 54 will be described. The method will be described with reference to the catheter 10 employing the centering balloon 44 as shown in FIG. 5. As shown in FIG. 7, the guidewire 40 is initially introduced into the vessel 54 so that it passes through the aneurysm 56. The catheter 10 is then advanced along the guidewire 40 while held within the third member 50 until a proximal end 58 of the aneurysm 56 is reached. Conventional fluoroscopy procedures are employed to visualize the radiopaque markers 18, 26 and the aneurysm 56. The catheter 10 is adjusted until the radiopaque marker 18 is aligned with a target location at the proximal end 58 of the aneurysm 56. Preferably, the target location will be at about 0.5 cm to 10 cm from the aneurysm 56. Such a distance provides sufficient space for placement of a proximal end of a graft. As shown in FIG. 8, the third elongate member 50 can optionally be radially expanded or have a malecot actuated to center the catheter 10 within the vessel 54.

With the radiopaque marker 18 at the proximal end 58 of the aneurysm, the second elongate member 20 is distally advanced relative to both the first and third elongate members 12, 50. The second elongate member 20 tracks along the guidewire 40 as it passes through the aneurysm 56. While the second elongate member 20 is being distally advanced through the aneurysm 56, the centering balloon 44 is inflated. The proximal end 46 of the balloon 44 has a nominal diameter corresponding substantially to the diameter of the vessel 54 which assists in centering the catheter 10 at the proximal end 58 of the aneurysm 56.

Figure 10:
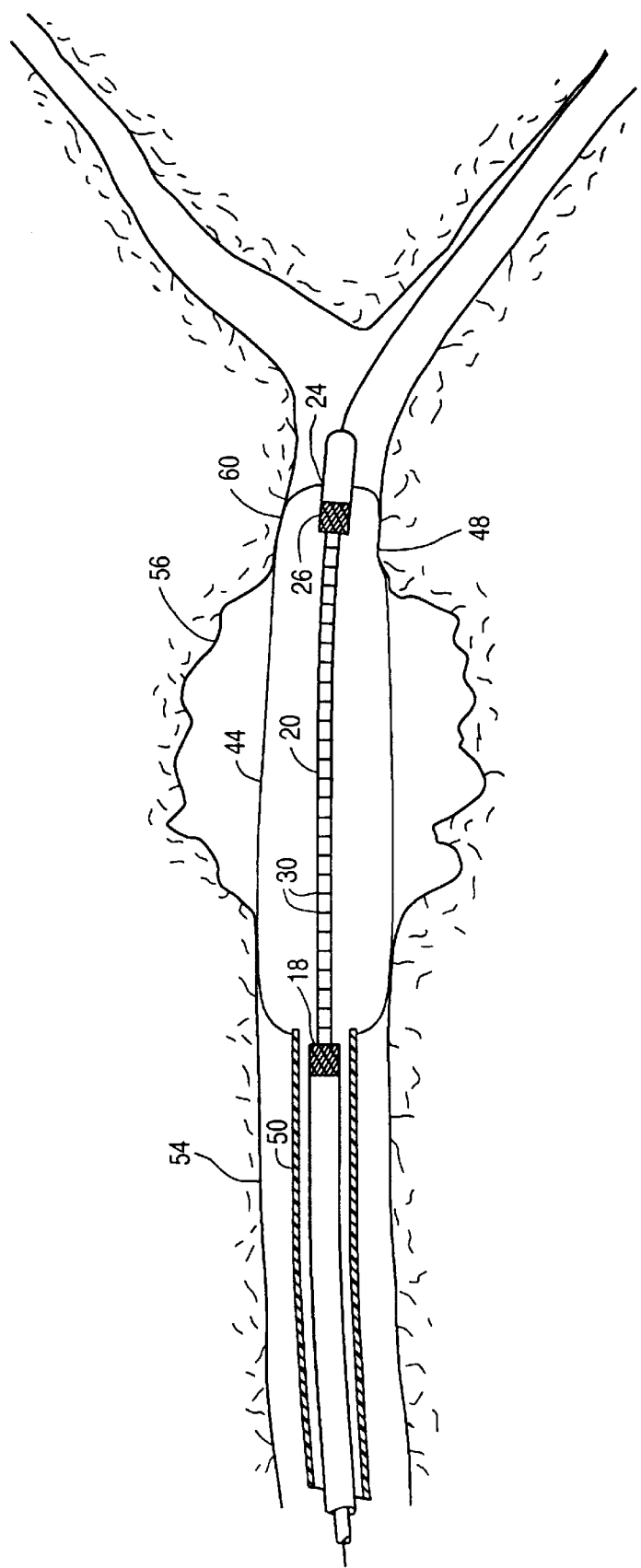

The second elongate member 20 is advanced further until the radiopaque marker 26 reaches a distal end 60 of the aneurysm 56 (see FIG. 10). The point at which the radiopaque marker 26 reaches the distal end 60 can be determined fluoroscopically. Alternatively, ultrasonic imaging can be used to assist in locating the markers 18, 26 relative to the ends of the aneurysm 56. The distal end 48 of the balloon 44 serves to center the catheter 10 on the opposite side of the aneurysm 56. In this way, the second elongate member 20 extends substantially along a geometric center of the vessel 54. This ensures accurate measurement of the length of the aneurysm 56 regardless of its geometric path through the patient's vascular anatomy.

Figure 11:
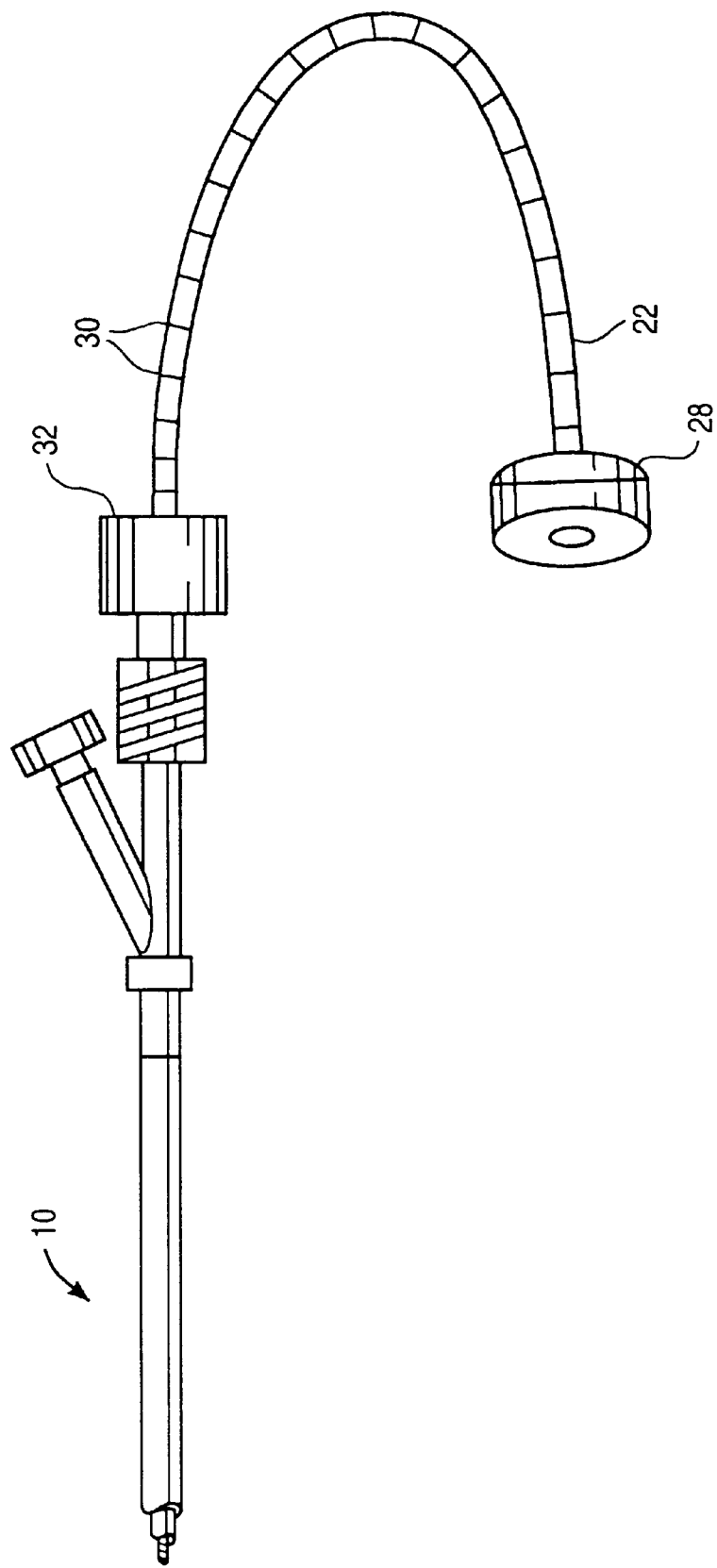

Once the markers 18, 26 have been aligned with the proximal and distal ends 58, 60 of the aneurysm 56, the distance between the markers 18, 26 can be visually determined. According to one method, the calibration marks 30 near the distal end 24 of the second elongate member 20 can be counted while the catheter remains in the patient. This can be accomplished by having radiopaque calibration marks 30 which can be counted using fluoroscopy. Alternatively, the first and second elongate members 12, 20 can be secured relative to each other and removed from the patient. The calibration marks 30 between the markers 18, 26 can then be counted. Yet a further alternative is shown in FIG. 11. According to this method, the calibration marks 30 between the valve 32 and the pull knob 28 can be counted. Such a procedure is advantageous in that the catheter 10 can remain within the patient's body while the marks 30 are counted.

Figure 12:
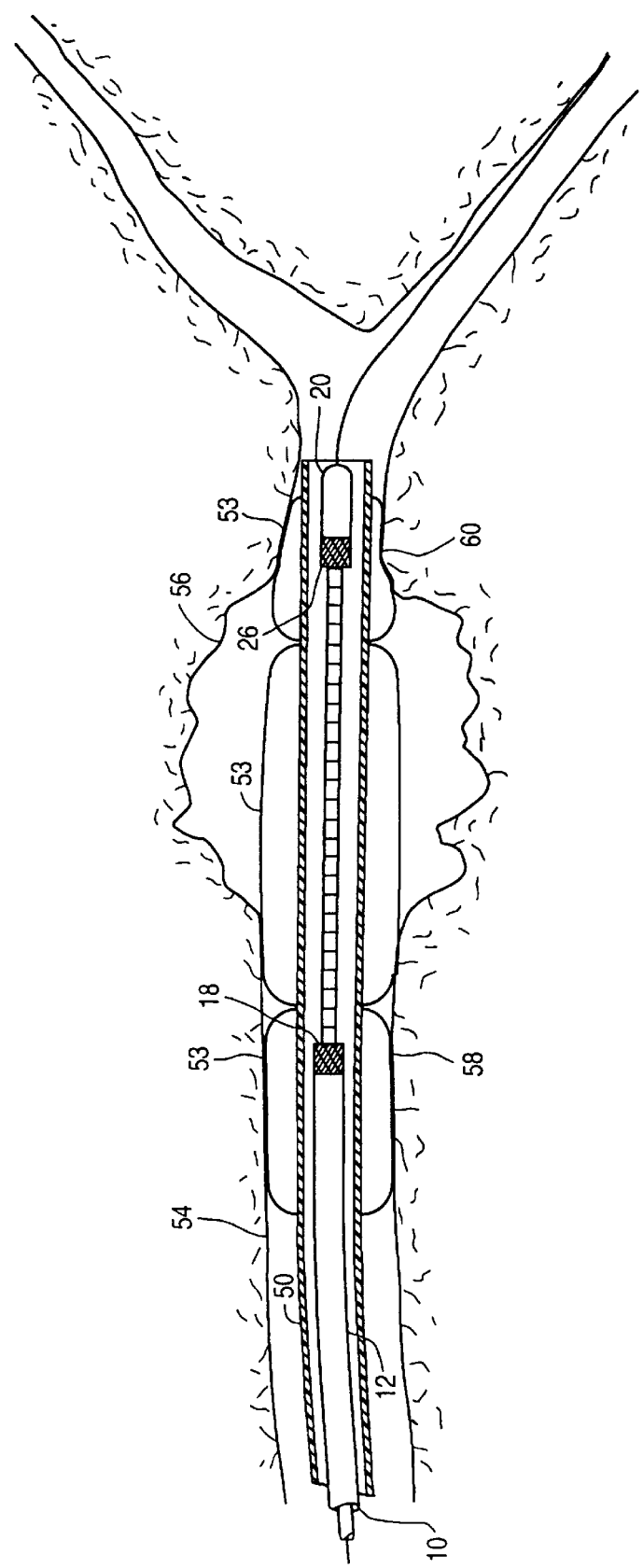
FIG. 12 illustrates an alternative method for measuring the length of a lesion in a blood vessel using the catheter and tubular member of FIG. 6.

As previously described, a variety of centering procedures can be employed to center the catheter 10 within the vessel 54. FIG. 12 illustrates an alternative method for centering the catheter 10 using the plurality of centering balloons 53. In this procedure, the third elongate member 50 is advanced entirely through the aneurysm 56. At or near the time when the third elongate 50 is being advanced, the balloons 53 are inflated to center the catheter 10 within the vessel 54. Once the third elongate member 50 has been advanced through the aneurysm 56, the first and second elongate members 12, 20 are translated relative to each other to align the markers 18, 26 with the proximal and distal ends 58, 60 of the aneurysm 56. Once properly aligned, determination of the axial distance between the markers 18, 26 can be determined as previously described.

Figure 13:
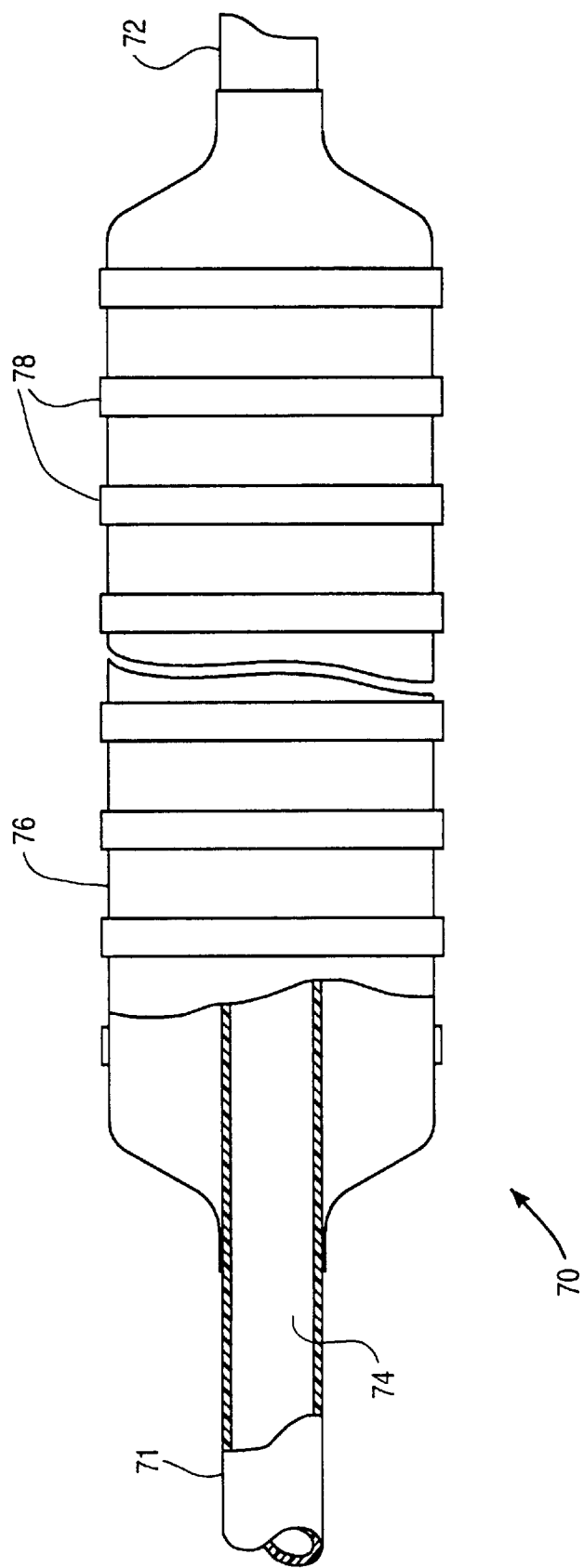
FIG. 13 illustrates an alternative embodiment of a luminal lesion catheter according to the present invention.

A further exemplary embodiment of a luminal lesion catheter 70 is shown in FIG. 13. The catheter 70 includes a catheter body 71 having a proximal end (not shown), a distal end 72, and a central lumen 74. Disposed over the body 71, preferably near the distal end 72, is a balloon 76. In one embodiment, the balloon 76 is inelastic and is preferably constructed of a material having a high modulus of elasticity such as PET. Alternatively, the balloon 76 can be elastic. Disposed over the balloon 76 are a plurality of concentric markers 78. The markers 78 are constructed of a material that is radio and/or fluoroscopically opaque, such as gold or barium sulfate. The markers 78 each have the same diameter, and preferably the same with, when the balloon 76 is inflated. The markers 78 are equally spaced-apart over the balloon 76. In this way, the catheter 70 can be inserted into a body lumen until the balloon 76 is within a lesionous area. The balloon 76 can then be inflated and the lesionous area radiographically or fluoroscopically imaged to produce an image of the lesionous area and the markers 78. The length of the lesion can then be determined by counting the number of markers between the ends of the lesion.

A further advantage of the catheter 70 is that both the diameter and the orientation of the markers 78 in the lumen can be determined. For example, an ultrasonic imaging transducer can be inserted through lumen 74 where it can be rotated to determine the diameter of the markers 78 and the distance between each of the markers 78. Ultrasound can be used with either an elastic or an inelastic balloon 76. Use of ultrasound is advantageous in providing excellent data acquisition. The resulting dimensions can then be used to construct a dimensionally significant graphical representation, such as a three dimensional wireframe model, of the markers 78. Such a model would yield the length, diameter, and radius or curvature of the body lumen and could be used in the selection of an appropriately sized prosthetic device, such as a stent graft for treating aneurysmal disease.

Figure 14:
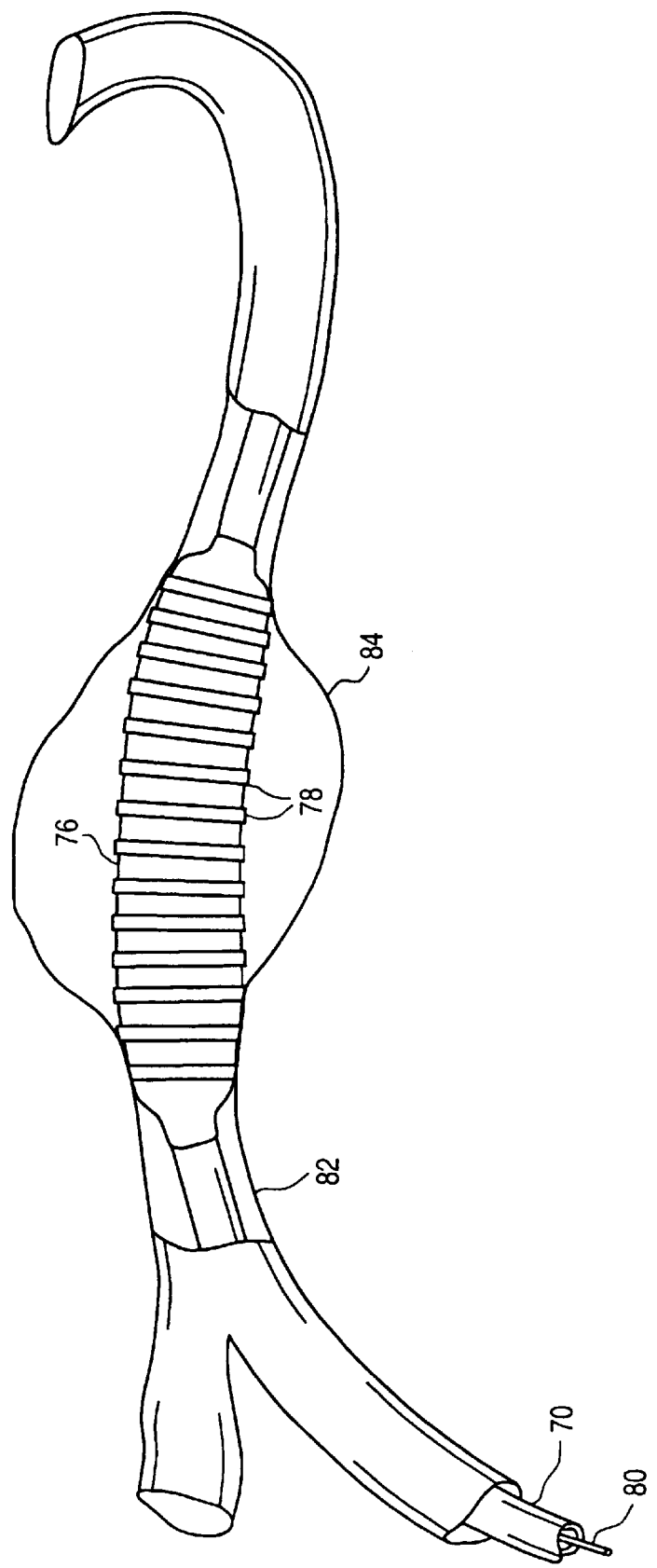
FIG. 14 illustrates an exemplary method for measuring a luminal lesion using the catheter of FIG. 13.

Referring to FIG. 14, an exemplary method for using the catheter 70 to measure the size of a body lumen will be described. Initially, a guidewire 80 is inserted into a body lumen, such as an artery 82. The catheter 70 is then introduced over the guidewire 80 until the balloon 76 passes through a lesion 84, with the markers 78 overlapping both ends of the lesion 84 as shown in FIG. 14. The balloon 76 is then inflated to position the catheter 70 within the artery 82. Radiographic or fluoroscopic imaging of the artery 82 is then performed to produce an image of the markers 78 and the lesion 84. In one particularly preferable aspect, imaging occurs by rotating an ultrasonic transducer within the lumen 74 (see FIG. 13) to produce an interior image of the markers 78. In this way, the length of the lesion 84 can be measured by counting the number of markers 78 lying between the ends of the lesion. Further, the diameter of the markers 78 can individually be determined. As the transducer is translated through the lumen 74, the distance between the markers 78 can also be measured so that the relative orientation of the markers 78 within the vessel 82 can be determined. By producing measurements corresponding to the diameter of each of the markers 78 and their orientation, a three dimensional image, such as a wireframe model, can be developed. Such a model is useful in accurately selecting an appropriately sized prosthetic device.

Although the foregoing invention has been described in some detail by way of illustration and example, for purposes of clarity of understanding, it will be obvious that certain changes and modifications may be practiced within the scope of the appended claims.

What is claimed is:

1. A method for measuring the distance between a first target location and a second target location within a lumen, said method comprising aligning a first marker on a first elongate member disposed within the lumen with the first target location;

aligning a second marker on a second elongate member disposed within the lumen with the second target location; and measuring the distance between the first and second markers, which measured distance corresponds to the distance between the first and second target locations;

wherein the lumen is a blood vessel lumen and the first and second target locations correspond to the ends of a lesion to determine the length of the lesion;

wherein aligning each marker comprises manually translating the elongate members carrying the markers within the lumen;

said method further comprising intraluminal ultrasonic imaging of the lumen, wherein the first and second markers are ultrasonically opaque and aligning said markers comprises alignment of the ultrasonic images of each marker with one end of the lesion.

2. A method for measuring the distance between a first target location and a second target location within a lumen, said method comprising aligning a first marker on a first elongate member disposed within the lumen with the first target location;

aligning a second marker on a second elongate member disposed within the lumen with the second target location; and measuring the distance between the first and second markers, which measured distance corresponds to the distance between the first and second target locations;

wherein measuring the distance between the first and second markers comprises visually observing calibration marks on one member relative to a reference location on the other member;

wherein the calibration marks are observed after the members are withdrawn from the lumen; and said method further comprising locking together the elongate members after aligning their respective markers and withdrawing the members from the body lumen prior to measuring the distance between the markers.

3. A method for measuring the distance between a first target location and a second target location within a lumen, said method comprising aligning a first marker on a first elongate member disposed within the lumen with the first target location;

aligning a second marker on a second elongate member disposed within the lumen with the second target location; and measuring the distance between the first and second markers, which measured distance corresponds to the distance between the first and second target locations;

wherein the lumen is a blood vessel lumen and the first and second target locations correspond to the ends of a lesion to determine the length of the lesion; and said method further comprising selecting the length of a vascular graft or stent so that it is sufficiently long to extend over the length of the lesion.

4. A luminal lesion measurement catheter comprising:

a first elongate member having a proximal end, a distal end, and a radiopaque marker near the distal end; and a second elongate member slidably received relative to the first member and having a proximal end, a distal end, and a radiopaque marker near the distal end, wherein the second member has a length greater than that of the first member and axially spaced-apart calibration marks which permit direct visual a reading of the axial distance between the radiopaque markers on the first and second members.

5. A catheter as in claim 4, wherein the first member is a tubular sleeve having a central passage wherein the length of the tubular sleeve is in the range from 40 cm to 200 cm.

6. A catheter as in claim 4, wherein the second member is a tubular body having a central guidewire lumen and a length in the range from 41 cm to 220 cm, wherein said calibration marks are visible on the outside surface of the tubular body.

7. A catheter as in claim 6, wherein the calibration marks are of the distal end of the tubular body.

8. A catheter as in claim 6, wherein the calibration marks are of the proximal end of the tubular body.

9. A catheter as in claim 5, further comprising a sealing valve at the proximal end of the tubular sleeve.

10. A catheter as in claim 4, further comprising a third elongate member slidably received relative to the first and second members and having a proximal end, a distal end, and a central lumen for receiving the first and second members.

11. A catheter as in claim 10, further comprising at least one balloon on said third elongate member for centering said third member within a blood vessel lumen.

12. A catheter as in claim 11, wherein the balloon is attached to the distal end of said third member and near the distal end of said second member, whereby inflation media can be introduced to the balloon through the central lumen of said third member.

13. A catheter as in claim 10, wherein the third member is radially expandable near its distal end for centering said third member within a blood vessel lumen.

14. A luminal lesion measurement catheter comprising:

an elongate catheter body having a proximal end, a distal end and a central lumen;

a balloon around the catheter body and near the distal end; and a plurality of spaced-apart concentric markers around the periphery of the balloon, the markers being radio or fluoroscopically opaque.

15. A catheter as in claim 14, wherein the markers are equally spaced-apart on the balloon and have a constant width.

16. A catheter as in claim 14, wherein the markers are constructed of gold.

17. A catheter as in claim 14, wherein the markers are constructed of barium sulfate.

18. A catheter as in claim 14, wherein the balloon is constructed of an elastic or an inelastic material.

* * * * *